United States Patent [19]

Verdon et al.

[11] Patent Number: 4,994,264
[45] Date of Patent: Feb. 19, 1991

[54] PRESS MOLDED COSMETIC COMPOSITION WITH PAY OFF

[75] Inventors: Debra Verdon, Leonardo, N.J.; Ivonne Brown, Roosevelt, N.Y.

[73] Assignee: Revlon, Inc., New York, N.Y.

[21] Appl. No.: 451,204

[22] Filed: Dec. 15, 1989

[51] Int. Cl.$^5$ ............... A61K 7/02; A61K 7/021; A61K 7/035
[52] U.S. Cl. .......................... 424/63; 424/69
[58] Field of Search ..................... 424/63, 69

[56] References Cited

U.S. PATENT DOCUMENTS

| 2,749,277 | 6/1956 | Toulmin | 424/69 X |
|---|---|---|---|
| 3,800,034 | 3/1974 | Kircher et al. | 424/69 X |
| 3,900,569 | 8/1975 | Monti | 514/780 |
| 3,978,207 | 8/1976 | Fotiu et al. | 424/63 |
| 3,987,204 | 10/1976 | Monti | 514/780 |
| 4,279,890 | 7/1981 | Harris et al. | 424/69 |
| 4,305,931 | 12/1981 | Kawano et al. | 424/69 |
| 4,358,286 | 11/1982 | Grollier et al. | 424/74 X |
| 4,459,285 | 7/1984 | Grollier et al. | 424/74 |
| 4,495,079 | 1/1985 | Good | 252/106 |
| 4,495,177 | 1/1985 | Taracatac et al. | 424/647 |
| 4,534,963 | 8/1985 | Gordon | 424/69 |
| 4,569,839 | 2/1986 | Grollier et al. | 424/74 |
| 4,581,230 | 4/1986 | Grollier et al. | 424/74 |
| 4,591,502 | 5/1986 | Schlossman | 424/69 X |
| 4,609,545 | 9/1986 | Schlossman | 424/69 X |
| 4,650,672 | 3/1987 | Yagita et al. | 424/69 |
| 4,659,562 | 4/1987 | Arraudeau et al. | 424/63 |
| 4,659,571 | 4/1987 | Laba | 424/65 |
| 4,724,138 | 2/1988 | Duffy et al. | 424/63 |
| 4,767,618 | 8/1988 | Grollier | 424/74 |
| 4,772,331 | 9/1988 | Noguchi et al. | 424/69 |
| 4,783,333 | 11/1988 | Mercado et al. | 424/69 X |
| 4,800,076 | 1/1989 | Bhat et al. | 424/69 |

Primary Examiner—Thurman K. Page
Assistant Examiner—Susan S. Rucker

[57] ABSTRACT

Press molded cosmetic compositions are prepared by first forming a paste of the composition with the aid of a gum containing aqueous solution and then extruding, pressing and drying the composition into one or more various shapes.

12 Claims, No Drawings

PRESS MOLDED COSMETIC COMPOSITION WITH PAY OFF

BACKGROUND OF THE INVENTION

1. Field of the Invention

This invention relates to press molded cosmetic compositions with good color pay-off characteristics. The press molded products provide for a more facile use of the cosmetic composition and avoid the disadvantages resulting from the use of the cosmetic composition in loose powder form, e.g., messiness, loss of powder by spilling and other known disadvantages.

The cosmetic compositions of the present invention would include those commonly used as cheek rouge, face powders, blushes, eye shadow, highlights and fragrance beads.

2. Description of the Prior Art

The prior art has disclosed the preparation of powdered compressed cosmetics which require the use of special components and/or processing aids or conditions.

U.S. Pat. No. 3,800,034 discloses the preparation of sticks of pressed cosmetic powder which contain 40 to 90% chalk.

U.S. Pat. No. 3,978,207 discloses the preparation of pressed cosmetics having a frosted pearl effect and which contain about 30–90% of a nacreous material such as mica, bismuth oxychloride or mica coated with titanium dioxide or bismuth oxychloride U.S. Pat. No. 4,305,931 is directed to a compressed powder composition which requires the presence of a hydroxypropyl-etherified glycolipid ester to prevent cracking if the compressed powder is dropped or dried.

U.S. Pat. No. 4,358,286, U.S. Pat No. 4,459,285, U.S. Pat. No. 4,569,839, U.S. Pat. No. 4,581,230 and U.S. Pat. No. 4,767,618 disclose, in part, the preparation of various cosmetic preparations containing pulverized particles of flowers or plants with certain thickening agents.

U.S. Pat. No. 4,534,963 discloses high pearlescent pressed powder eye shadow compositions made with 40–80% of nacreous material and other components such as micronized polyethylene wax and certain tetra-esters.

U.S. Pat. No. 4,591,502 and U.S. Pat. No. 4,609,545 disclose the use of certain hydrocarbon waxes as compressing aids for cosmetic powders.

U.S. Pat No. 4,650,672 discloses a multicolored pressed cosmetic powder formed from grains of various pigments.

U.S. Pat. No. 4,659,562 discloses the use of an admixture of finely divided silica and finely divided polyethylene fibers as a binding agent for certain cosmetic formulations.

U.S. Pat. No. 4,724,138 discloses the use of calcium sulfate hemihydrate in the formation of a shaped pigmented cosmetic powder.

U.S. Pat. No. 4,772,331 discloses the use of colored flaky pigment compositions in cosmetics.

U.S. Pat. No. 4,783,333 discloses the use of stones or pearls of color coated titanated mica particles for eye shadow or blusher formulations.

SUMMARY OF THE INVENTION

The present invention relates to a novel press molded cosmetic composition having good color pay-off characteristics and formed from a paste comprising, in weight %, about 5 to 60%, and preferably about 20 to 35%, of water.

about 0.1 to 1.0%, and preferably about 0.1 to 0.3% of one or more water soluble hydrophillic colloids or gums, about 0.01 to 20%, and preferably about 0.1 to 5%, of one or more polar solvents other than water, about 0.2 to 5.0%, and preferably about 1.0 to 3.0%, of one or more wetting agents or surfactants, about 1.0 to 10.0%, and preferably about 2.0 to 5%, of one or more powdered lubricants, about 1.0 to 15.0%, and preferably about 5.0 to 10.0%, of one or more binding agents, The cosmetic compositions of the present invention may also contain, in weight %, about 1 to 10%, and preferably about 2 to 8%, of bismuth oxychloride (BIOCl), about 0 to 50%, and preferably about 0 to 30%, of one or more cosmetic coloring agents, about 0 to 90%, and preferably about 0 to 30%, of one or more cosmetic fillers, about.0.01 to 5%, and preferably about 1 to 2%, of one or more preservatives, about 0.01 to 5%, and preferably about 1 to 2%, of one or more fragrances oils, about 0.01 to 0.10%, and preferably about 0.01 to 0.05%, of one or more antioxidants, and about 0.10 to 15%, and preferably about 0.5 to 5%, of one or more cosmetic emollients.

The total weight % of the composition is 100%.

An object of the present invention is to provide cosmetic compositions in a form which will provide for good pay-off properties.

A further object of the present invention is to provide cosmetic compositions in various pressed forms.

DETAILED DESCRIPTION OF THE PREFERRED EMBODIMENT

The water which is used in the compositions of the present invention is preferably deionized or distilled water, although tap water can be used with preservatives.

The hydrocolloid gums which may be used in the compositions of the present invention would include
Acacia,
Agar,
Algin,
Alginic Acid,
Ammonium Alginate,
Calcium Alginate,
Calcium Carrageenan,
Carboxymethyl Hydroxyethylcellulose,
Carboxymethyl Hydroxypropyl Guar,
Carrageenan,
Cellulose Gum,
Damar,
Dextran,
Dextrin,
Ethylcellulose,
Gelatin,
Guar Gum,
Guar Hydroxypropyltrimonium Chloride,
Gum Benzoin,
Hydroxybutyl Methylcellulose,
Hydroxyethylcellulose,
Hydroxyethyl Ethylcellulose, Hydroxypropylcellulose,
Hydroxypropyl Guar,
Hydroxypropyl Methylcellulose,
Jalap Resin,
Karaya Gum,
Kelp,
Locust Bean Gum,
Maltodextrin,
Methylcellulose,
Olibanum,
Pectin,
Potassium Alginate,
Potassium Carrageenan,
Propylene Glycol Alginate,
Sandarac Gum,
Sodium Carboxymethyl Dextran,
Sodium Carrageenan,
Sodium Cellulose Sulfate,
Tragacanth Gum, and
Xanthan Gum.

Xanthan gum is the preferred of such materials.

The polar solvents other than water which may be used in the compositions of the present invention would include alcohols and glycols such as ethanol, isopropanol, propylene glycol, glycerine and polyethylene glycol, and mixtures thereof. Ethanol is the preferred of such polar solvents.

The wetting agents which may be used in the compositions of the present invention include one or more of all those found useful for such purposes in the cosmetic arts, including all those listed as surfactant-emulsifying agents on pages 90-94 of the *CTFA Cosmetic Ingredient Handbook*, 1st Edition, 1988, (Editor, J. M. Nikitakis,, the contents of which are hereby incorporated herein by reference.

The powdered lubricants which may be used in the compositions of the present invention would include aluminium starch octenylsuccinate, teflon, L-laureth lycine, polyethylene, nylon and polymethylmethacrylate, and mixtures thereof. The preferred of such lubricants is aluminum starch octenylsuccinate.

The binding agents which may be used in the compositions of the present invention would include kaolin, bentonite, metallic stearates such as zinc stearate (which is normally a mixture of the zinc salts of stearic acid and palmitic acid), lithium stearate, calcium stearate and magnesium stearate, calcium silicate, cellulose gum, corn starch, methyl cellulose, L-laureth lycine, rice starch, boron nitride, and xanthan gum. The compressing aid compositions disclosed in U.S. Pat. Nos. 4,591,502 and 4,609,545 may also be used. The preferred binding agent is kaolin.

The coloring agents which may be used in the compositions of the present invention would include I/O (iron oxide) colors, ultramarine colors, manganese violet, carmine, ferricyanides, FD&C colors and D&C colors.

The cosmetic fillers which may be used in the compositions of the present invention would include talc, mica, TiO$_2$ coated mica and zinc oxide. Talc and mica are the preferred of such fillers.

The preservatives which may be used in the compositions of the present invention would include methyl paraben, butyl paraben, propyl paraben and phenoxyethanol.

The antioxidants which may be used in the compositions of the present invention would include butylated hydroxy anisole (BHA) and butylated hydroxy toluene (BHT).

The emollients which may be used in the compositions of the present invention would include all those useful as such in the cosmetic arts, and including all those listed on pages 80-81 of the *CTFA Cosmetic Ingredient Handbook*, 1st Edition, 1988, (Editor J. M. Nikitakis), the contents of which are hereby incorporated by reference. The preferred of such emollients are octyl palmitate and triisocetyl citrate.

The pressed cosmetic compositions can be prepared and sold in various shapes and/or containers, such as in the form of sticks, tablets, pellets and others shapes.

In preparing the pressed compositions, a slurry is prepared from the water, gum and polar solvent. The slurry contains about 20 ± 2% of the polar solvent other than water and about 80 ± 8% of a solution of the gum in water which contains about 0.25 ± 0.025% of the gum.

About 20 to 50%, and preferably 20 to 35%, weight % of the slurry is then uniformly mixed with about 50 to 80%, and preferably about 65 to 80%, of an admixture of the other components of the composition to form a homogenous paste. In forming the paste, wetting agent and the polar solvent assist in the dispersion of the water throughout the paste. The paste is formed at ambient temperatures of about 25 ± 5° C.

The paste is then extruded at a temperature of about 10° to 35° C. in a standard cosmetic powder compression molding device under standard cosmetic powder molding conditions.

The composition is molded into the desired shape and then removed from the compression molding device and dried at a temperature of about 40° to 55° C. to a final moisture content of about 0.25 to 7%.

The resulting shaped products can be used to apply either a primary or secondary powder coating to the skin with good pay-off properties. The choice of coloring agents which can be used in the cosmetic formulations of the present invention provides freedom to create various looks and unique designs on the skin. The aluminum starch octenylsuccinate aids in providing color pay off. The BIOCl aids in the application of the shaped composition to the skin.

The following example is merely illustrative of the scope of the present invention and is not intended as a limitation upon the scope thereof.

EXAMPLE

The following formulation was used to make a paste which was then extruded, press molded and dried as described above to produce pellets that measured about ¼"×½" in diameter and which has good color pay-off properties when applied to the skin as a primary or secondary powder cosmetic.

A slurry was first formed from 20% by weight of ethanol and 80% by weight of a 0.25% by weight solution of xanthan gum in water.

A paste was then formed from 27.3 grams of the slurry and 72.7 grams of the powder components of the composition which were present as follows before and after drying:

| Powder Component | Wt. W/No H$_2$O Weight % | W/H$_2$O Theoretical |
|---|---|---|
| Talc | 33.30 | 24.14 |
| Aluminum starch | 5.00 | 3.64 |

-continued

| Powder Component | Wt. W/No H₂O Weight % | W/H₂O Theoretical |
|---|---|---|
| octenylsuccinate | | |
| Phenoxyethanol | 1.00 | 0.73 |
| Methyl paraben | 0.20 | 0.15 |
| Propyl paraben | 0.10 | 0.07 |
| Mica | 1.00 | 0.73 |
| an admix of BIOCl/TiO₂/mica | 5.00 | 3.64 |
| Zinc oxide | 2.00 | 1.50 |
| I/O black | 0.20 | 0.15 |
| Red No. 6 Ca Lake | 0.15 | 0.11 |
| I/O maroon | 7.50 | 5.45 |
| Kaoline | 10.00 | 7.27 |
| Ultramarine blue | 0.30 | 0.22 |
| Cloisonne red (TiO₂/Mica/Carmine 40) | 19.00 | 13.81 |
| Superpearl 100 (TiO₂/Mica) | 10.00 | 7.27 |
| Octylpalmitate | 1.25 | 0.91 |
| Triisocetyl citrate | 1.00 | 0.73 |
| Polyglyceryl-3-diisostearate (wetting agent) | 3.00 | 2.18 |
| Water Slurry | | 27.3 |
| | 100.00 | 100.00 |

The resulting product was a pinkish colored block or pellet intended for blush application users.

What is claimed is:

1. A press molded cosmetic composition having good pay-off characteristics and formed from a paste comprising, in weight %,
   about 5 to 60% of water,
   about 0.1 to 1.0% of one or more hydrocolloid gums,
   about 0.01 to 20% of one or more polar solvents other than water,
   about 0.2 to 5.0% of one or more wetting agents,
   about 0.1 to 10% of one or more powdered lubricants, and
   about 10 to 90% of one or more binders.

2. A press molded cosmetic composition formed from a paste as in claim 1 and further comprising
   about 0.1 to 10% of bismuth oxychloride,
   about 0 to 50% of one or more cosmetic coloring agents,
   about 0 to 90% of one or more cosmetic fillers,
   about 0.01 to 5% of one or more preservatives,
   about 0.01 to 0.10% of one or more antioxidants,
   about 0.1 to 15% of one or more cosmetic emollients, and
   about 0.01 to 5% of one or more fragrance oils.

3. A press molded cosmetic composition formed from a paste as in claim 1 and wherein
   said gum comprises xanthan gum,
   said polar solvent comprises an alcohol,
   said wetting agent comprises polyglyceryl-3-diisostearate
   said powdered lubricant comprises aluminum starch octenylsuccinate, and
   said binder comprises kaolin.

4. A press molded cosmetic composition as in claim 1 in the form of a pellet.

5. A press molded cosmetic composition as in claim 2 in the form of a pellet.

6. A press molded cosmetic composition as in claim 3 in the form of a pellet.

7. A process for forming a press molded cosmetic composition with good pay-off characteristics which comprises forming a paste of said composition from a slurry of water, gum, polar solvent other than water and the remaining components of said cosmetic composition,
extruding said paste into an extrudate
press molding said extrudate, and
drying the press molded material.

8. A process as in claim 7 in which said paste comprises, in weight %,
   about 5 to 60% water,
   about 0.1 to 1.0% gum, and
   about 0.01 to 20% polar solvent other than water.

9. A process as in claim 8 in which said paste further comprises
   about 0.2 to 5% of one or more wetting agents,
   about 0.1 to 10% of one or more powdered lubricants,
   about 1 to 15% of one or more binders,
   about 1 to 10% of bismuth oxychloride,
   about 0 to 50% of one or more cosmetic coloring agents,
   about 0 to 90% of one or more cosmetic fillers,
   about 0.01 to 5% of one or more preservatives,
   about 0.01 to 0.10% of one or more antioxidants,
   about 0.1 to 15% of one or more cosmetic emollients, and
   about 0.01 to 5% of one or more fragrance oils.

10. A process as in claim 7 in which the cosmetic composition is press molded into the form of pellets.

11. A press molded cosmetic composition having good pay-off characteristics and formed from a paste comprising, in weight %,
    about 5 to 60% water,
    about 0.1 to 1.0% of one or more hydrocolloid gums,
    about 0.01 to 20% of one or more polar solvents other than water selected from the group consisting of ethanol, isopropanol, propylene glycol, glycerine, polyethylene glycol, or mixtures thereof,
    about 0.2 to 5.0% of one or more wetting agents,
    about 0.1 to 10% or one or more powdered lubricants selected from the group consisting of aluminum starch octenylsuccinate, teflon, L-laureth lycine, polyethylene, nylon, polymethacrylate, and mixtures thereof, and
    about 10-90% of one or more binders selected from the group consisting of kaolin, bentonite, zinc stearate, lithium stearate, calcium stearate, magnesium stearate, calcium silicate, cellulose gum corn starch, methyl cellulose, L-laureth lycine, rice starch, or boron nitride.

12. A press molded cosmetic composition formed from a paste as in claim 1 and further comprising
    about 0.1 to 10% bismuth oxychloride,
    about 0 to 50% of one or more cosmetic coloring agents,
    about 0 to 90% of one or more cosmetic fillers selected from the group consisting of talk, mica, TiO₂, coated mica, or zinc oxide,
    about 0.01 to 5% of one or more preservatives which are methylparaben, butyl paraben, propyl paraben, or phenoxyethanol,
    about 0.01 to 0.10% of one or more antioxidants selected from the group consisting of BHA or BHT,
    about 0.1 to 15% of one or more cosmetic emollients, and
    about 0.01 to 5% of one or more fragrance oils.

* * * * *